United States Patent [19]

Engelhardt et al.

[11] Patent Number: 5,041,496

[45] Date of Patent: Aug. 20, 1991

[54] HYDROPHILIC, SWELLABLE GRAFT COPOLYMERS, THEIR PREPARATION AND USE

[75] Inventors: Friedrich Engelhardt; Ulrich Riegel, both of Frankfurt am Main; Jürgen Kühlwein, Offenbach am Main, all of Fed. Rep. of Germany

[73] Assignee: Cassella AG, Frankfurt am Main, Fed. Rep. of Germany

[21] Appl. No.: 495,642

[22] Filed: Mar. 19, 1990

[30] Foreign Application Priority Data

Apr. 1, 1989 [DE] Fed. Rep. of Germany ....... 3910563

[51] Int. Cl.$^5$ .................... C08F 283/02; C08F 283/06
[52] U.S. Cl. ........................................ 525/41; 525/42; 525/404; 525/445
[58] Field of Search .................... 525/404, 445, 41, 42

[56] References Cited

U.S. PATENT DOCUMENTS 3,900,378 8/1975 Yen ....................................... 522/78
4,931,497 6/1990 Engelhardt ............................ 525/42

Primary Examiner—Patricia Short
Attorney, Agent, or Firm—Connolly and Hutz

[57] ABSTRACT

The present invention relates to hydrophilic, swellable graft copolymers composed, in random distribution, of 0.5 to 20% by weight of radicals of the general formula I

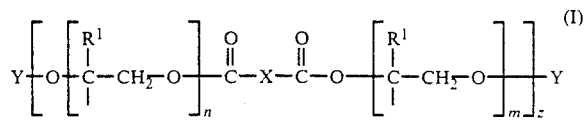

of 79 to 99% by weight of radicals containing an acidic group, of the general formula II

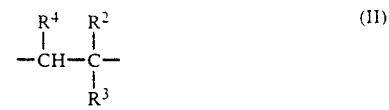

and of 0.1 to 2% by weight of radicals of a crosslinking agent which are derived from monomers having at least two olefinically unsaturated double bonds, and the radicals X, Z, m, n, z and also $R^1$ to $R^4$ are defined as given in the description, a process for the preparation of these graft copolymers and also their use as absorbents for water and aqueous solutions.

17 Claims, No Drawings

HYDROPHILIC, SWELLABLE GRAFT COPOLYMERS, THEIR PREPARATION AND USE

The present invention relates to hydrophilic, swellable graft copolymers composed, in random distribution, of 0.5 to 20% by weight of radicals of the general formula I

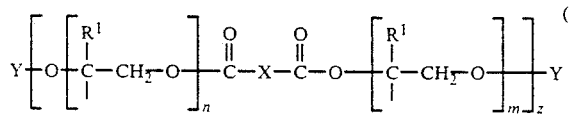

of 79 to 99% by weight of radicals containing an acidic group, of the general formula II

and of 0.1 to 2% by weight of radicals of a crosslinking agent which are derived from monomers having at least two olefinically unsaturated double bonds, where X denotes $(C_1-C_6)$-alkylene, $(C_1-C_6)$-alkenyl, phenylene or sulphonyl-substituted phenylene,

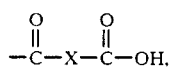

Y denotes hydrogen or z denotes 1 to 100, m and n independently of one another denote 2 to 300, $R^1$ denotes hydrogen or methyl, $R^2$ denotes hydrogen, methyl or ethyl, $R^3$ denotes the carboxyl group, the sulphonyl group, the phosphonyl group, which may optionally be esterified with an alkanol having 1 to 4 carbon atoms, or denotes a group of the formula

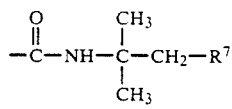

in which $R^7$ represents the sulphonyl group or the phosphonyl group, $R^4$ denotes hydrogen, methyl, ethyl or the carboxyl group, and also to their preparation and use as absorbents for water and aqueous solutions, for example in sanitary items, for soil improvement or as filtration auxiliaries.

Swellable polymers which absorb aqueous solutions are used for preparing tampons, diapers, sanitary towels and other sanitary items and also as water-retaining agents in market gardening.

Known absorption resins of this type include crosslinked carboxymethylcellulose, partially crosslinked polyalkylene oxide, hydrolysates of starch-acrylonitrile graft copolymers and salts of partially crosslinked polyacrylic acid.

However, these known polymers have disadvantages in particular in the case of absorption of aqueous electrolyte solutions and also blood and urine.

The current state of the art produces high absorbency only with inadequate gel stabilities in the swollen polymer particles. Tacky materials are formed which impair the absorbency of the products made from them.

It is known that increasing the crosslink density improves the gel stability and the rate of liquid uptake but results in a simultaneous fall in the absorption capacity. This measure is unhelpful in that the absorption capacity is the most important property of the polymer.

The object of the present invention is to provide modified polymers which absorb aqueous solutions, have a high absorption rate and form, in the swollen state, non-tacky hydrogel particles of high gel stability.

Surprisingly, it has now been found that the desired range of properties is achieved by the graft copolymers according to the invention, since the macromolecular network of these polymers physically brings about an increase in the gel stability or gel strength of the swollen polymer and also an improved electrolyte tolerance.

Preference is given to products according to the invention which are composed of 0.5 to 15% by weight of radicals of the general formula I, 84 to 99% by weight of radicals of the general formula II and 0.1 to 1.8% by weight of crosslinking structures derived from monomers having at least two olefinically unsaturated double bonds.

Particular preference is given to products according to the invention composed of 1 to 10.5% by weight of radicals of the general formula I, 88 to 98.5% by weight of radicals of the general formula II and 0.3 to 1.5% by weight of crosslinking structures derived from monomers having at least two olefinically unsaturated double bonds.

In the graft copolymers according to the invention, the radicals of the general formula I may all have exactly the same structure, but they may also differ with regard to the radical $R^1$ and/or with regard to the numbers m and n. For instance, $R^1$ may at random be hydrogen or methyl, or else there may be sequences of relatively large polymer segments in which $R^1$ is in each case hydrogen only or methyl only.

The diol components in the radicals of the general formula I are preferably derived from polyethylene glycols with a molecular weight from 100 to 8000, polypropylene glycols with a molecular weight from 140 to 8000, products composed randomly of ethylene glycol units and propylene glycol units having a molecular weight from 130 to 10000, and block copolymers composed of ethylene glycol units and propylene glycol units having a molecular weight from 130 to 10000.

X preferably denotes $(C_1-C_6)$-alkylene, ethenyl, 1,4-phenylene, 1,3-phenylene or 5-sulpho-1,3-phenylene. z preferably denotes 2 to 50.

$R^2$ in the radicals of the general formula II preferably denotes hydrogen or methyl. $R^3$ preferably represents the carboxyl group, the sulphonyl group or the phosphonyl group. Particular preference is given to the carboxyl group. $R^4$ preferably denotes hydrogen.

The abovementioned crosslinking structures may be derived from any suitable monomers having at least two olefinically unsaturated double bonds.

Examples of suitable monomers are compounds containing at least two alkenyl groups, for example vinyl or allyl, or at least two alkenoyl groups, for example acrylate or methacrylate.

The crosslinking structures are preferably derived from monomers containing 2, 3 or 4 ethylenically unsaturated double bonds.

Particular preference is given to crosslinking structures derived from trimethylolpropane triacrylate, tetraallyloxyethane or methylenebisacrylamide.

Most particular preference is given to graft copolymers according to the invention containing a plurality of the abovementioned preferred or particularly preferred features.

The graft copolymers according to the invention can be prepared by known polymerization processes. Preference is given to polymerization in aqueous solution by the process known as gel polymerization. In this process, 15–50% strength aqueous solutions of the comonomers are polymerized using suitable known catalyst systems without mechanical agitation using the Trommsdorff-Norrish effect (Bios Final Rep. 363.22; Makromol. Chem. 1, 169 (1947)).

The polymerization reaction can be carried out in the temperature range between 0° C. and 130° C., preferably between 10° C., and 100° C., and either at atmospheric pressure or under elevated pressure. The polymerization can, as normal, also be carried out in an inert gas atmosphere, preferably under nitrogen.

Initiation of the polymerization can be brought about by high-energy electromagnetic radiation or by the usual chemical polymerization initiators, for example organic peroxides such as benzoyl peroxide, tert-butyl hydroperoxide, methyl ethyl ketone peroxide, cumene hydroperoxide, azo compounds such as azo diisobutyronitrile and also inorganic peroxide compounds such as $(NH_4)_2S_2O_8$ or $K_2S_2O_8$ or $H_2O_2$ optionally as a combination with reducing agents such as sodium hydrogen sulphite and iron(II) sulphate or redox systems containing, as reducing agent, an aliphatic and aromatic sulphinic acid, such as benzenesulphinic acid and toluenesulphinic acid or derivatives of these acids such as for example Mannich adducts of sulphinic acid, aldehydes and amino compounds as described in DE-C-1,301,576. As a rule, for every 100 g of total monomers, 0.03 to 2 g of the polymerization initiator are used.

Post-heating of the polymer gels for several hours in the temperature range 50°–130° C., preferably 70°–100° C., gives a further improvement in the qualities of the polymers.

The copolymers according to the invention which have been prepared by this method and are in the form of aqueous jellies can be obtained in solid form after mechanical comminution with suitable equipment and drying by known processes and be used in this form.

Graft copolymers according to the invention are consequently advantageously obtained if 0.5 to 20% by weight, preferably 0.5 to 15, in particular 1 to 10.5% by weight of a polyalkylene oxide compound of the general formula Ia

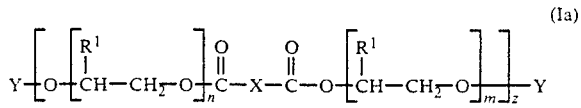

79 to 99% by weight, preferably 84 to 99, in particular 88 to 98.5% by weight of an unsaturated acid of the general formula IIa

or an alkali metal salt, ammonium salt or amine salt thereof and 0.1 to 2% by weight, preferably 0.1 to 1.8, in particular 0.3 to 1.5% by weight of a monomer having at least two olefinically unsaturated double bonds, where the radicals $R^1$ to $R^4$, X, Y and the numbers m, n and z have the meanings given above, are reacted under the conditions of gel polymerization.

The polyalkylene oxide compounds of the general formula Ia can be obtained by a simple esterification reaction between acids of the general formula III

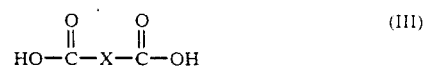

in which X is defined as above, or suitable derivatives thereof, and polyalkylene oxides. Examples of suitable polyalkylene oxides are polyethylene glycol, polypropylene glycol, block copolymers composed of polyethylene oxide blocks and polypropylene oxide blocks and also random ethylene oxide/propylene oxide copolymers.

The monomers of the formula (IIa) are known compounds such as for example acrylic acid, methacrylic acid, vinylsulphonic acid, maleic acid, fumaric acid, crotonic acid, 2-acrylamido-2-methylpropanesulphonic acid, 2-acrylamido-2-methylpropanephosphomic acid and vinylphosphonic acid and also the semiesters thereof.

The polyolefinic monomers used as crosslinking agents are standard products. Examples are bisacrylamidoacetic acid, trimethylolpropane triacetate and tetraallyloxyethane.

The graft copolymers according to the invention are eminently suitable as absorbents for water and aqueous solutions so that they can be used advantageously as a water-retaining agent in market gardening, as a filtration auxiliary and in particular as an absorbent component in sanitary items such as diapers, tampons or sanitary towels.

The following examples describe the preparation of the graft copolymers according to the invention.

EXAMPLE 1

A 10-liter-capacity polyethylene bucket which has been well insulated with expanded plastic material is initially charged with 5169 g of deionized water, then 1000 g of sodium bicarbonate are dispersed in the water and 1888 g of acrylic acid are slowly metered in so that excessive foaming of the reaction solution is avoided, the reaction solution being cooled to a temperature of about 12°–10° C. Then 100 g of the reaction product according to Example a (see below) serving as the graft base, 12 g of trimethylolpropane triacrylate and 10 g of sodium diisooctylsulphosuccinate (Rewopol V 2133 supplied by REWO, Steinau) are added. At a temperature of 10°–12° C., the initiators a redox system consisting of 2.2 g of 2,2'-azobisamidinopropane dihydrochloride dissolved in 20 g of water, 4.4 g of potassium peroxydisulphate dissolved in 170 g of water, and 6 g of sodium pyrosulphite dissolved in 120 g of water are added in succession and stirred well. The reaction solution is then left to stand without stirring and the polymerization which commences, resulting in an increase in the temperature up to about 85° C., produces a solid gel. This is then mechanically comminuted, dried at temperatures of above 80° C. and ground.

The product described above was incorporated by prior art methods into a baby-diaper and gave particularly good liquid retention.

Preparation of the hydrophilic polyester serving as the graft base:

EXAMPLE A

Process A 2025 g (1.35 mol) of polyethylene glycol 1500 are melted in a 4-liter flask and then 513.7 g (6.75 mols) of 1,2-propanediol, 786.5 g (4.05 mol) of dimethyl terephthalate and 1.15 g (0.004 mol) of titanium (IV) isopropanolate are added with stirring. The reaction mixture is then heated to 180° C. with stirring and while passing through a gentle stream of nitrogen. The methanol resulting from the reaction which now commences is distilled off through a packed column with a distillation attachment. The reaction temperature is increased until 328 ml of methanol have been collected.

The packed column is then exchanged for a descending condenser with a graduated receiver Then at 230° C. the pressure is reduced over a period of 2–3 hours to 60 mbar and sufficient excess 1,2-propanediol is distilled off until the reaction material has a hydroxyl number of 53 and a carboxyl number of 1 or below.

EXAMPLE B

Process B

A 4-liter flask is initially charged with 2228.6 g (21 mol) of diethylene glycol and 600 g (1 mol) of polyethylene glycol 600 at 100° C. and then 830.6 g (5 mol) of isophthalic acid, 664.6 g (4 mol) of terephthalic acid, 268.2 g of sodium salt 5-sulphoisophthalate (SIA) (1 mol) and 2.68 g (1% by weight relative to the SIA) of anhydrous sodium carbonate are then added with stirring. The reaction mixture is then heated to 190° C. while stirring and passing through a gentle stream of nitrogen. The water resulting from the reaction which now commences is separated off via a packed column with a distillation attachment. The reaction temperature is increased until 360 g of water have been distilled off.

The packed column is then exchanged for a descending condenser with a graduated receiver. After setting the pressure to 1 mbar, the temperature is increased to 280° C. in the course of 3 hours and kept at this temperature until the reaction material has a hydroxyl number of 15 and a carboxyl number of 2 to 3.

EXAMPLE C

Process C 300g (0.1 mol) of polyethylene glycol 3000 are melted in a 0.5-liter flask and then 44.04 g of poly(1,4-butylene terephthalate) and 57 mg (0.0002 mol) of titanium (IV) isopropanolate are added with stirring. The reaction mixture is then heated to 260° C. while stirring and passing through a gentle current of nitrogen. These conditions are maintained until the depolymerization occurring has resulted in the polybutylene terephthalate dissolving completely and until the reaction material has a hydroxyl number of 32 and a carboxyl number of 2 or below.

EXAMPLE D

Process D

A 0.5-liter flask is initially charged with 250 g (0.25 mol) of polyethylene glycol 1000 and 49.03 g (0.5 mol) of maleic anhydride at room temperature. The reaction mixture is heated to 80° C. while a gentle current of nitrogen gas is passed through and, after melting of the polyethylene glycol, is stirred until the maleic anhydride has completely dissolved in a weakly exothermic reaction. Stirring is then maintained for a further hour under these conditions. The resulting reaction material has a carboxyl number of 100 and a hydroxyl number of 4.

EXAMPLE E

Process E

This azeotropic esterification process is particularly suitable for the preparation of polycondensation compounds from oxyalkylated fatty amines, diols and aliphatic dicarboxylic acids and has been disclosed in the two publications DE-A1-3,526,600 and DE-A1-3,526,601.

Table 1 lists other graft bases.

| Polycondensate example | Polydiol molecular weight components | | | Mol ratio diol Polydiol | Dicarboxylic acid | OH number | Carboxyl number | Process |
| --- | --- | --- | --- | --- | --- | --- | --- | --- |
| | POE | POP | Diol | | | | | |
| f | 1500 | — | PPD-1.2 | 3:1 | TPA | 53 | 0, 6 | A |
| g | 850 | 1750 | DEG | 3:1 | TPA | 30 | 1, 5 | A |
| h | 1750 | 1750 | PPD-1.2 | 3:1 | TPA | 27 | 0, 8 | A |
| i | 3800 | 950 | MEG | 2, 5:1 | TPA | 19 | 2, 5 | A |
| j | 3000 | — | MEG | 3:1 | TPA | 28 | 4 | A |
| k | 600 | — | DEG | 9:1 | TPA/IPA/SIA 4:5:1 | 15 | 2, 5 | B |
| l | 300 | 300 | DEG | 9:1 | TPA/IPA/SIA 4:5:1 | 12 | 2 | B |
| m | 3000 | — | BD-1.4 | 2:1 | TPA | 32 | 2 | C |
| n | 3800 | 950 | MEG | 2, 5:1 | TPA | 20 | 1, 5 | C |
| o | 1000 | — | — | — | MA | 4 | 90 | D |
| p | — | 1750 | — | — | MA | 1, 5 | 56 | D |

-continued

| Polycondensate example | Polydiol molecular weight components POE | POP | Diol | Mol ratio diol Polydiol | Dicarboxylic acid | OH number | Carboxyl number | Process |
|---|---|---|---|---|---|---|---|---|
| q | 1750 | 1750 | — | — | MA | 1.2 | 30 | D |

POE = polyoxyethylene
POP = polyoxypropylene
PPD-1.2 = 1,2-propanediol
DEG = diethylene glycol
MEG = monoethylene glycol
Bd-1.4 = 1,4-butanediol
TPA = terephthalic acid
IPA = isophthalic acid
SIA = 5-sulphoisophthalic acid
MA = Na salt of maleic anhydride

EXAMPLE 2

A 10-liter plastic bucket is initially charged with 4419 g of ice and 1888 g of acrylic acid and then 1573 g of 50% strength NaOH solution is slowly metered in followed by 100 g of the reaction product according to Example 1b serving as the graft base, 12 g of bisacrylamidoacetic acid dispersed in 100 g of water and dissolved by adding NaOH and brought to a pH of 6, and 10 g of Rewopol V 2133 are added. The reaction solution is brought to a temperature of 20° C. and then the initiators, a redox system consisting of 6 g of potassium peroxydisulphate dissolved in 170 g of water and 0.15 g of ascorbic acid dissolved in 120 g of water are added and the mixture is left to stand without stripping. The gel resulting from polymerization is then mechanically comminuted, dried at temperatures above 80° C. and ground.

EXAMPLE 3

A 10-liter polyethylene bucket is initially charged with 5250 g of deionized water, 1888 g of acrylic acid and 100 g of the reaction product according to Example 1c serving as the graft base. Then 12 g of tetraallyloxyethane are added with stirring. After bringing the reaction solution to 18°–20° C., the initiators consisting of 6 g of potassium peroxydisulphate in 170 g of water and 0.2 g of ascorbic acid in 20 g of water are added in succession and the reaction vessel is left to stand without stirring in a well insulated condition. After the reaction has commenced, the temperature increases to about 90° C. and a solid gel results. This is comminuted mechanically using an extruder, to which 1555 g of 50% strength NaOH are continuously metered in causing partial evaporation of the water. The polymer flakes are then finally dried at temperatures of above 80° C. and ground.

Other examples of the preparation of graft copolymers according to the invention and according to the Examples 1 and 2 described here are summarized in the following table. The percentages are by weight relative to the proportion of total monomers.

The following abbreviations are used:
AS: acrylic acid
MAS: methacrylic acid
CTS: crotonic acid
VPS: vinylphosphonic acid
VPE: semi-ester of vinylphosphonic acid
AMPS: 2-acrylamido-2-methylpropanesulphonic acid
AMPP: 2-acrylamido-2-methylpropanephosphonic acid
BAAE: bisacrylamidoacetic acid
TMPTA: trimethylolpropane triacrylate
TAE: tetraallyloxyethane

| Example | Prepared according to Example | AS (%) | MAS (%) | AMPS (%) | AMPP (%) | VPS (%) | VPE (%) | CTS (%) | Graft base according to Example | (%) | BAAE (%) | TMPTA (%) | TAE (%) | (L10748a) Degree of neutralization (%) |
|---|---|---|---|---|---|---|---|---|---|---|---|---|---|---|
| 4 | 1 | 94.4 | | | | | | | 1d | 5 | 0.6 | | | 45 |
| 5 | 1 | 94.4 | | | | | | | 1e | 5 | 0.6 | | | 45 |
| 6 | 1 | 89.4 | | | | | | | 1f | 10 | 0.6 | | | 45 |
| 7 | 1 | 94.4 | | | | | | | 1g | 5 | 0.6 | | | 45 |
| 8 | 1 | 94.4 | | | | | | | 1h | 5 | 0.6 | | | 45 |
| 9 | 1 | 94.4 | | | | | | | 1i | 5 | 0.6 | | | 45 |
| 10 | 1 | 88.5 | | | | | | | 1j | 10 | 1.5 | | | 70 |
| 11 | 1 | 94.4 | | | | | | | 1k | 5 | 0.6 | | | 45 |
| 12 | 2 | 89.4 | | | | | | | 1l | 10 | 0.6 | | | 75 |
| 13 | 2 | 89.4 | | | | | | | 1m | 10 | | | 0.6 | 78 |
| 14 | 1 | 98.4 | | | | | | | 1n | 1 | 0.6 | | | 45 |
| 15 | 1 | 70.0 | 10.0 | 9.5 | | | | | 1o | 10 | | | 0.5 | 48 |
| 16 | 2 | 65.0 | | 25.0 | | 4.0 | | | 1p | 5 | 1.0 | | | 45 |
| 17 | 2 | 75.0 | 5.0 | 10.0 | | | 4.2 | | 1q | 5 | | 0.8 | | 60 |
| 18 | 2 | 85.0 | | 5.0 | 4.5 | | | | 1a | 5 | 0.5 | | | 70 |
| 19 | 1 | 72.0 | | 20.0 | | 4.2 | | | 1a | 3 | 0.8 | | | 80 |
| 20 | 1 | 81.0 | 10.0 | | | | 4.0 | | 1a | 4 | | 1.0 | | 36 |
| 21 | 2 | 90.0 | | | 4.6 | | | | 1a | 5 | | | 0.4 | 25 |
| 22 | 2 | 79.0 | | 19.0 | | | | | 1a | 1 | | 1.0 | | 40 |
| 23 | 1 | 72.0 | | 19.3 | | | | 5.0 | 1a | 3 | | | 0.7 | 48 |
| 24 | 1 | 90.0 | | | | 1.0 | | | 1a | 8 | | | 1.0 | 32 |

We claim:

1. Hydrophilic, swellable graft copolymers composed, in random distribution, of 0.5 to 20% by weight of radicals of the general formula I

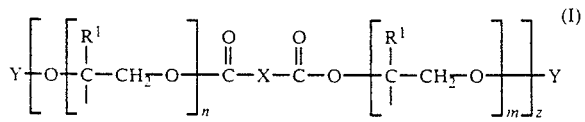

of 79 to 99% by weight of radicals containing an acidic group, of the general formula II

and of 0.1 to 2% by weight of radicals of a crosslinking agent which are derived from monomers having at least two olefinically unsaturated double bonds, where X denotes $(C_1-C_6)$-alkylene, $(C_1-C_6)$-alkenyl, phenylene or sulphonyl-substituted phenylene, Y denotes hydrogen or

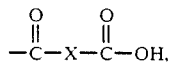

z denotes 1 to 100 m and n independently of one another denote 2 to 300, $R^1$ denotes hydrogen or methyl, $R^2$ denotes hydrogen, methyl or ethyl, $R^3$ denotes the carboxyl group, the sulphonyl group, the phosphonyl group, which may optionally be esterified with an alkanol having 1 to 4 carbon atoms, or denotes a group of the formula

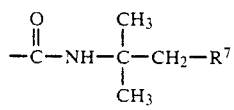

in which $R^7$ represents the sulphonyl group or the phosphonyl group, $R^4$ denotes hydrogen, methyl, ethyl or the carboxyl group.

2. Graft copolymers according to claim 1, characterized in that they are composed of 1 to 10.5% by weight of radicals of the general formula I 88 to 98.5% by weight of radicals of the general formula II and 0.3 to 1.5% by weight of crosslinking structures.

3. Graft copolymers according to claim 1, characterized in that the radicals of the general formula I differ with regard to radical $R^1$ and the numbers m and n.

4. Graft copolymers according to claim 1, characterized in that the radical $R^2$ in the general formula II denotes hydrogen or methyl, the radical $R^3$ denotes the carboxyl group, the sulphonyl group or the phosphonyl group and the radical $R^4$ denotes hydrogen.

5. Graft copolymers according to claim 1, characterized in that the radical $R^3$ of the general formula II denotes the carboxyl group.

6. Graft copolymers according to claim 1, characterized in that the crosslinking structures are derived from monomers having at least two alkenyl groups or at least two alkenoyl groups, 7. Graft copolymers according to claim 1, characterized in that X denotes $(C_1-C_6)$-alkylene, ethenyl, 1,4-phenylene, 1,3-phenylene or 5-sulpho-1,3-phenylene.

8. Process for the preparation of the graft copolymers claimed in claim 1, characterized in that 0.5 to 20% by weight of a polyalkylene oxide compound of the general formula Ia

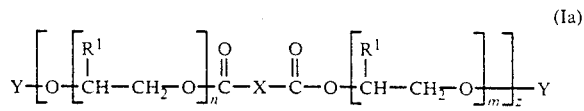

79 to 99% by weight of an unsaturated acid of the general formula IIa

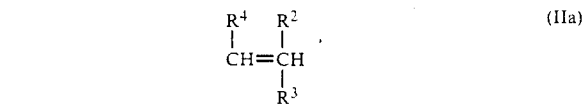

or an alkali metal salt, ammonium salt or amine salt thereof and 0.1 to 2% by weight of a monomer having at least two olefinically unsaturated double bonds, where the radicals $R^1$ to $R^4$, X, Y and the numbers m, n and z have the meanings give in claim 1, are reacted under the conditions of gel polymerization.

9. A process according to claim 8 wherein the amount of the polyalkylene oxide compound of the general formula Ia is 0.5 to 15% by weight.

10. A process according to claim 8 wherein the amount of the polyalkylene oxide compound of the general formula Ia is 1 to 10.5% by weight.

11. A process according to claim 8 wherein the amount an unsaturated acid of the general formula IIa is 84 to 99% by weight.

12. A process according to claim 8 wherein the amount an unsaturated acid of the general formula IIa is 88 to 98.5% by weight.

13. A process according to claim 8 wherein the amount of a monomer having at least two olefinically unsaturated double bonds is 0.1 to 1.8% by weight.

14. A process according to claim 8 wherein the amount of a monomer having at least two olefinically unsaturated double bonds is 0.3 to 1.5% by weight.

15. Graft copolymers according to claim 6 wherein said monomers are trimethylolpropane triacrylate, tetraallyloxyethane or methylenebisacrylamide.

16. Absorbents for water or aqueous solutions comprising the graft copolymers according to claim 1.

17. Diapers, tampons or sanitary towels comprising the graft copolymers according to claim 1.

* * * * *